US012558077B2

(12) United States Patent (10) Patent No.: US 12,558,077 B2
Ismic et al. (45) Date of Patent: Feb. 24, 2026

(54) TOOL ACTIVATION AND CONTROL FOR SURGICAL HANDPIECE

(71) Applicant: Arthrex, Inc., Naples, FL (US)

(72) Inventors: Dzenan Ismic, Oberndorf bei Salzburg (AT); Alexander Glaser, Munich (DE); Daniel Strömsdörfer, Neufahrn (DE)

(73) Assignee: Arthrex, Inc., Naples, FL (US)

( * ) Notice: Subject to any disclaimer, the term of this patent is extended or adjusted under 35 U.S.C. 154(b) by 236 days.

(21) Appl. No.: 18/380,752

(22) Filed: Oct. 17, 2023

(65) Prior Publication Data

US 2024/0122586 A1 Apr. 18, 2024

Related U.S. Application Data

(60) Provisional application No. 63/417,130, filed on Oct. 18, 2022.

(51) Int. Cl.
*A61B 17/00* (2006.01)

(52) U.S. Cl.
CPC .... *A61B 17/00* (2013.01); *A61B 2017/00367* (2013.01)

(58) Field of Classification Search
CPC ................ A61B 17/00; A61B 17/1626; A61B 2017/0036
See application file for complete search history.

(56) References Cited

U.S. PATENT DOCUMENTS

| | | | |
|---|---|---|---|
| 5,264,783 A | 11/1993 | Vig et al. | |
| 5,268,622 A | 12/1993 | Philipp | |
| 5,712,543 A | 1/1998 | Sjostrom | |
| 5,747,953 A | 5/1998 | Philipp | |
| 5,804,936 A | 9/1998 | Brodsky et al. | |
| 6,013,991 A | 1/2000 | Phillipp | |
| 6,960,894 B2 | 11/2005 | Carusillo et al. | |
| 7,638,958 B2 | 12/2009 | Philipp et al. | |
| 8,029,510 B2 | 10/2011 | Hoegerle | |
| 8,446,120 B2 | 5/2013 | Forster et al. | |
| 9,450,471 B2 | 9/2016 | Mergener et al. | |
| 9,787,159 B2 | 10/2017 | Beyerl | |
| 9,991,069 B2 | 6/2018 | Nicholas et al. | |
| 10,056,806 B2 | 8/2018 | Hatfield et al. | |
| 10,285,690 B2 | 5/2019 | Nicholas | |
| 10,456,122 B2 | 10/2019 | Koltz et al. | |
| 10,530,220 B2 | 1/2020 | Mergener et al. | |
| 11,110,583 B2 | 9/2021 | Fauteux et al. | |
| 2008/0077149 A1 | 3/2008 | Hoegerle | |
| 2012/0179148 A1* | 7/2012 | Conlon ................... F16H 19/06 | |
| | | | 606/1 |
| 2014/0012238 A1* | 1/2014 | Chen ...................... A61B 17/32 | |
| | | | 606/1 |
| 2022/0024018 A1 | 1/2022 | Benzing | |

FOREIGN PATENT DOCUMENTS

WO 2022159574 A1 7/2022

* cited by examiner

*Primary Examiner* — Scott Luan
(74) *Attorney, Agent, or Firm* — Price Heneveld LLP

(57) ABSTRACT

An actuation mechanism for a surgical handpiece includes a trigger assembly extending along a translational path and a rotational linkage in connection with the trigger assembly that converts translational motion along the translational path to a rotational motion about the actuation path. A magnet is in connection with the rotational linkage. The magnet has opposing poles that rotate in response to the rotational motion.

25 Claims, 8 Drawing Sheets

TOOL ACTIVATION AND CONTROL FOR SURGICAL HANDPIECE

CROSS-REFERENCE TO RELATED APPLICATIONS

This application claims priority under 35 U.S.C. § 119(e) and the benefit of U.S. Provisional Application No. 63/417, 130 entitled TOOL ACTIVATION AND CONTROL FOR SURGICAL HANDPIECE, filed on Oct. 18, 2022, by Ismic, et al., the entire disclosure of which is incorporated herein by reference.

BACKGROUND

The present disclosure generally relates to a control assembly for a surgical handpiece and, more particularly, to a trigger assembly and actuation mechanism for a surgical handpiece in the form of a motorized tool. Motorized tools may be implemented in a variety of medical or surgical procedures and provide improvements in patient treatments as well as outcomes. In various implementations, the disclosure provides for actuation mechanisms and sensor assemblies that may improve the operation of motorized surgical tools for various applications.

SUMMARY

The disclosure provides for an actuation mechanism and sensor configured to provide an input and control for a surgical handpiece or surgical tool. In various implementations, the actuation mechanism includes a translational trigger assembly that engages a rotational linkage to convert translational motion of the trigger to a rotational motion that may rotate on an axis defined by the actuation path. In order to detect the rotational position of the rotational linkage, a magnet may be connected to the rotational linkage opposite the trigger. In response to the depression of the trigger assembly, the rotational linkage may rotate the poles of the magnet about an axis parallel to the translational path, such that the rotational position of the magnetic poles may be detected to provide control of the surgical handpiece with a high level of control and accuracy. The actuation mechanism, including the trigger assembly and the rotational linkage, may be incorporated in a housing and connected to a body of the surgical handpiece. A magnetic sensor may further be incorporated in the body of the surgical handpiece and separated from the actuation mechanism via a wall of the body of the handpiece. The wall of the handpiece that separates the actuation mechanism from the magnetic sensor may provide a structural support as well as a protective enclosure to insulate the magnetic sensor and corresponding circuitry of the control circuit from the harsh external environment to which the actuation mechanism and the surgical handpiece may be exposed. As discussed in the following detailed examples, the combination of the improved accuracy provided by the actuation mechanism, as well as the robust and intuitive assembly of the magnetic sensor and control circuitry of the handpiece, may improve the operation and assembly of devices for a variety of applications.

These and other features, objects and advantages of the present disclosure will become apparent upon reading the following description thereof together with reference to the accompanying drawings.

DETAILED DESCRIPTION OF THE PREFERRED EMBODIMENT

In the following description of the preferred implementations, reference is made to the accompanying drawings, which show specific implementations that may be practiced. Wherever possible, the same reference numbers will be used throughout the drawings to refer to the same or like parts. It is to be understood that other implementations may be utilized and structural and functional changes may be made without departing from the scope of this disclosure.

Figure 1:
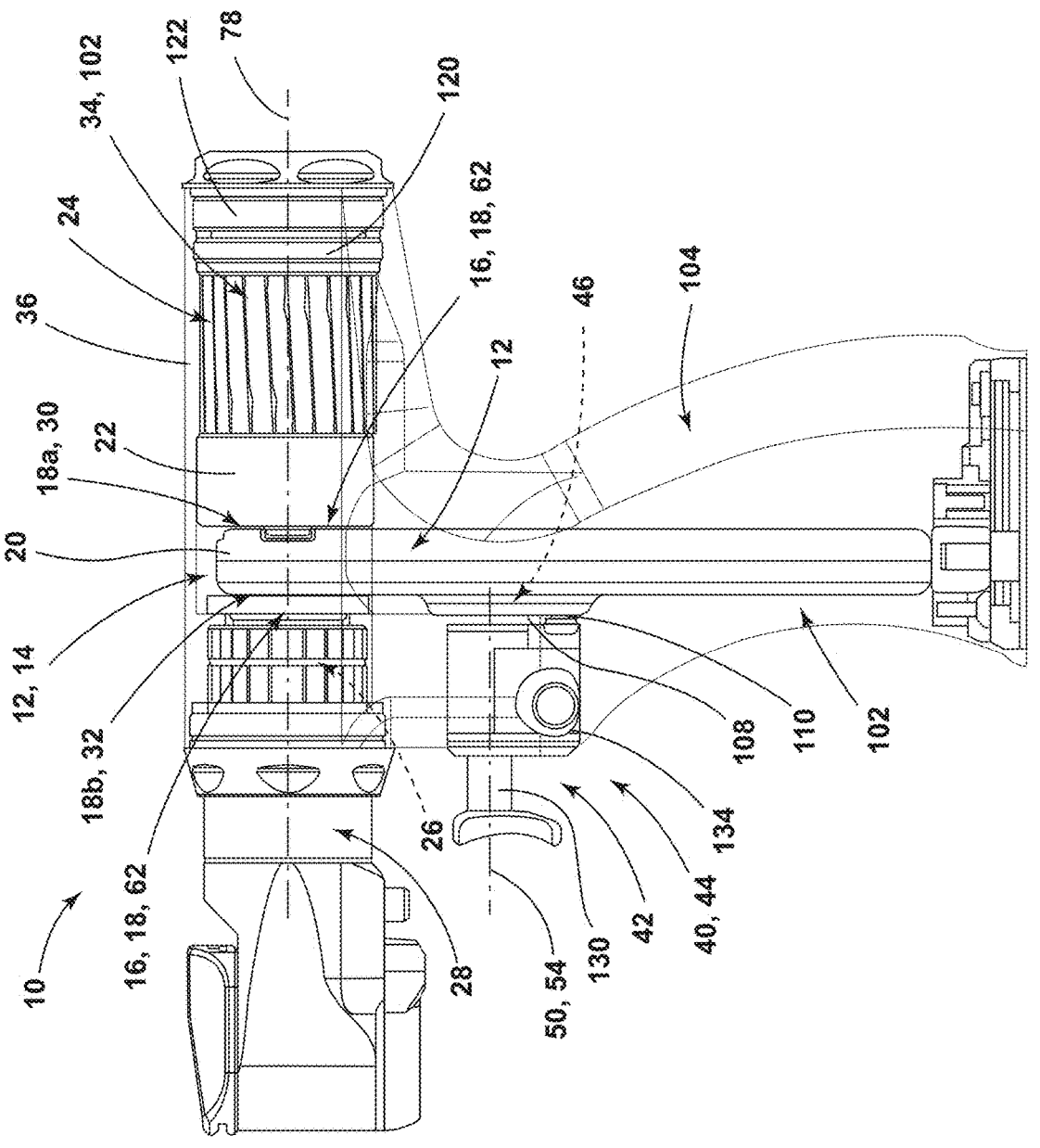
FIG. 1 is a partially-transparent side view of a surgical handpiece.

Referring to FIG. 1, a partially transparent, side view of a surgical handpiece 10 is shown demonstrating a variety of features discussed in the following disclosure. In various implementations, the disclosure provides for a control circuit or control module 12 that may improve the assembly, operation, and longevity of the handpiece 10. As demonstrated, the control module 12 may be sealed in a potted or encapsulated assembly 14 that may include a plurality of positioning features 16 disposed on a first side 18a and an opposing second side 18b of a collar 20 of the encapsulated assembly 14. In this configuration, the positioning features 16 on the opposing sides 18 of the collar 20 may engage and mechanically align the collar 20 with a stator assembly 22 of an electric motor 24 on the first side 18a and a drive coupling assembly 26 of a drive head 28 of the surgical handpiece 10 on the second side 18b. As further discussed in reference to FIGS. 2-4, the first side 18a of the control module 12 may engage the stator assembly 22 via a stator interface 30, and the second side 18b of the control module 12 may engage the drive head 28 of the surgical handpiece 10 via a drive-side interface 32. In this configuration, the disclosure may provide for various improvements related to the assembly of the surgical handpiece 10, including the improved fixation and alignment of the control module 12 within an interior cavity 34 of the surgical handpiece.

As later discussed in reference to FIGS. 5 and 6, the disclosure further provides for an actuation mechanism 40 comprising a trigger assembly 42 that may provide for a user input or control interface 44 configured to control the operation of the surgical handpiece 10. In operation, the actuation mechanism 40 may wirelessly communicate a positioning indication representative of a magnitude of a user input to the trigger assembly 42 to a position sensor 46 of the control module 12. In various implementations, the actuation mechanism 40 may comprise a rotational linkage 48 in connection with the trigger assembly 42 that may convert a translational motion of the trigger assembly 42 along a translational path 50 to a rotational motion that may follow a rotational or helical path 52. In operation, the rotational linkage 42 may cause a rotation of a portion of the actuation mechanism rotating about a trigger axis 54 that may extend parallel to the translational path 50. As a result of the rotational motion of the rotational linkage 48, a sensor magnet 56 may be rotated about the trigger axis 54, such that the corresponding change in orientation of a plurality of poles 58 may be detected by the position sensor 46 of the control module 12. Accordingly, the disclosure may provide for features that may be implemented in a variety of combinations to improve the operation and assembly of the surgical handpiece 10.

Figure 2:
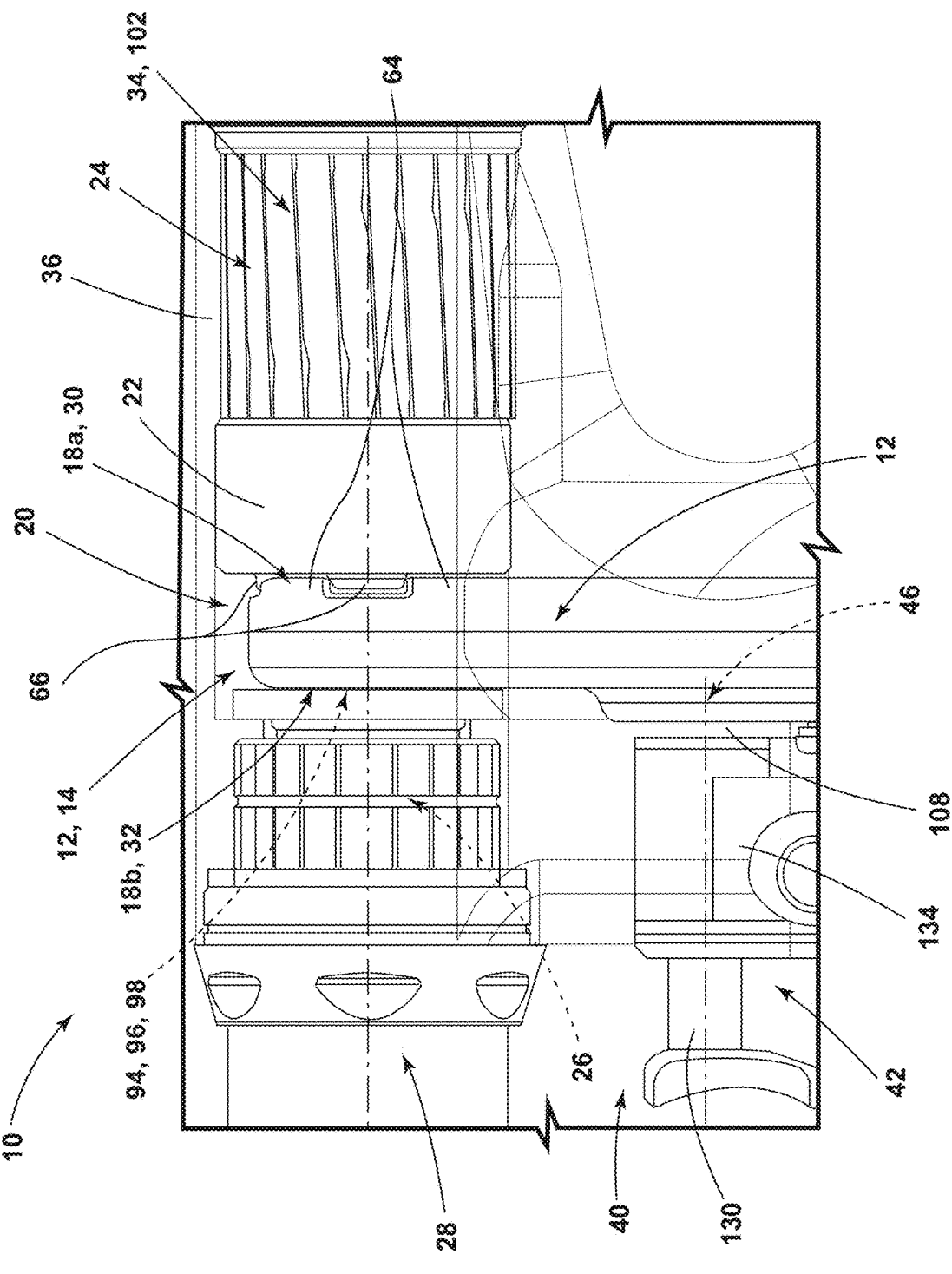
FIG. 2 is a detailed side view of a surgical handpiece demonstrating engaging interfaces configured to position an electronic control circuit and a stator assembly within a body of a surgical handpiece.
Figure 3A:
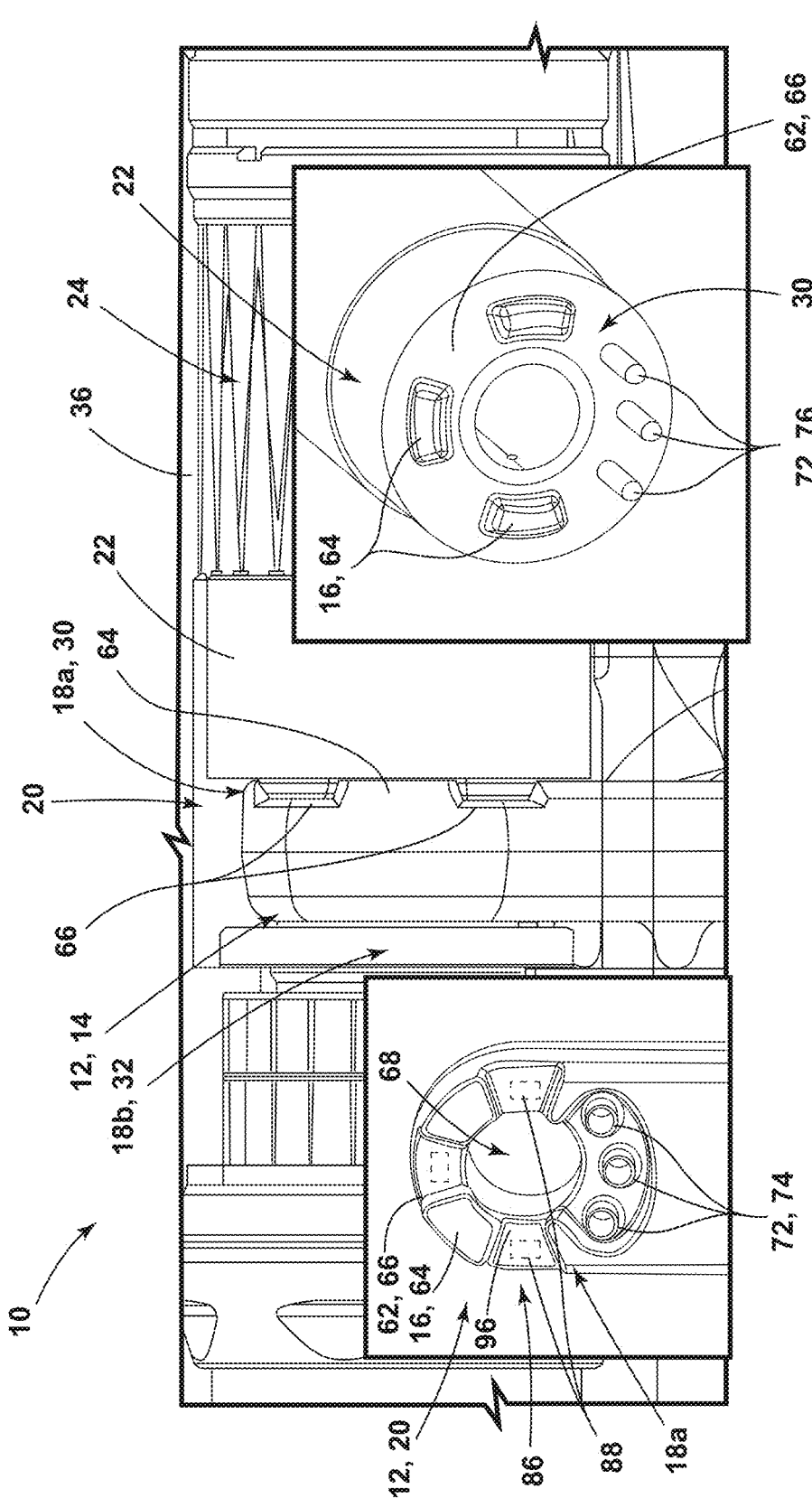
FIG. 3A demonstrates detailed projected views of an engaging interface between a control circuit and a stator assembly.
Figure 3B:
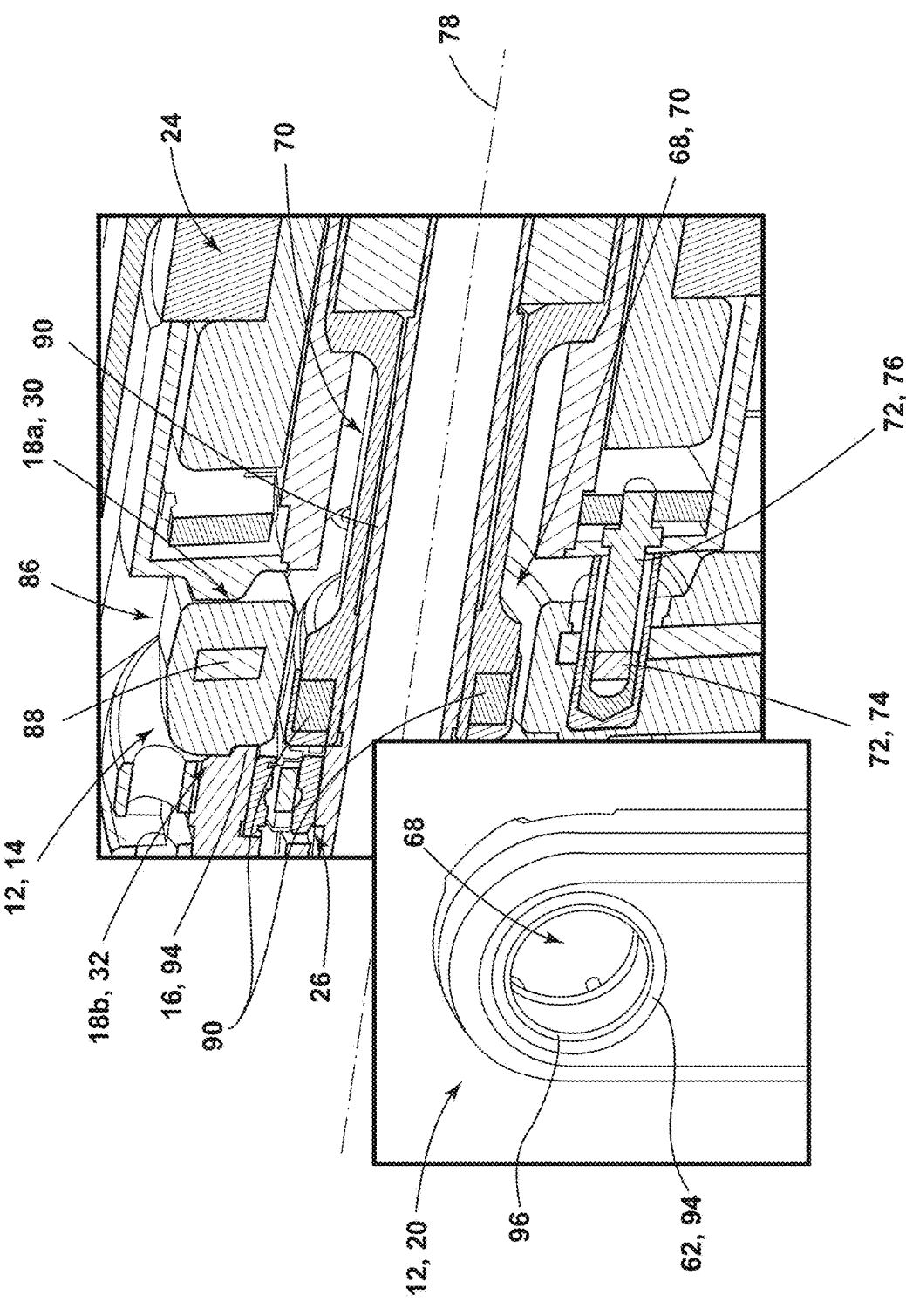
FIG. 3B demonstrates detailed projected views of an engaging interface between a control circuit and a drive side coupling assembly or drive head of the surgical handpiece.

Referring now to FIGS. 2, 3A, and 3B, further details of the positioning features 16 and assembly of the encapsulated assembly 14 with the electric motor 24 and the drive head 28 of the surgical handpiece 10 are discussed. As demonstrated in FIG. 3A, a detailed view of the first side 18a of the collar 20 is shown demonstrating the positioning features 16. Additionally, FIG. 3A demonstrates a detailed view of the stator interface 30, including complementary retention features 62 that align and engage with the positioning features 16 of the control module 12. In various implementations, the positioning feature 16 and the complementary retention features 62 may correspond to lobes or protrusions 64 and receiving notches 66 that may be distributed in an alternating and mating pattern across the first side 18a of the collar 20 and the opposing stator interface 30 of the stator assembly 22. As shown, the lobes 64 and receiving notches 66 may generally be wedge-shaped, having corresponding widths that increase in proportion radially outward from an opening 68 formed through the collar 20. In this configuration, the wedge-shaped lobes 64 and corresponding receiving notches 66 may align the collar opening 68 formed through the collar 20 with a drive aperture 70 and output shaft or drive shaft 80 (see FIG. 3B) driven by a rotor of the electric motor 24.

In addition to aligning the opening 68 with the drive aperture 70 to pass the drive shaft 80 in connection with the drive coupling assembly 26, the positioning features 16 and complementary retention features 62 may align a conductive interface 72 of the control module 12 with the stator assembly 22. In the example shown, the conductive interface 72 comprises a plurality of pin connectors 74 formed on the first side 18a of the control module 12 and a plurality of complementary conductive pins 76 protruding from the stator interface 30 of the stator assembly 22. In the assembled configuration, the conductive interface 72 may conductively connect a motor switching circuit enclosed within the control module 12 with the conductive stator windings of the electric motor 24. Accordingly, the alignment of the collar 20 with the stator assembly 22 may provide for a conductive connection between the control circuitry (e.g., a control circuit and motor switching circuit) of the control module 12 and the motor 24 as well as mechanically align the drive shaft 80 of the electric motor 24 with the opening 68 formed by the collar 20.

Referring now to FIG. 3B, a detailed cross-sectional view of the control module 12 is shown demonstrating the conductive pins 76 of the stator assembly 22 engaging a complementary pin connector 74 formed by the conductive interface 72 on the first side 18a of the control module 12. In the example shown, the conductive pins 76 may correspond to spring pins that extend perpendicular from the surface forming the stator interface 30 and approximately parallel to a drive axis 78 of the drive shaft 80. In addition to the conductive interface 72, the cross-sectional view of the surgical handpiece 10 further demonstrates a shaft rotation sensor 86 formed by a magnetic sensor array 88 configured to detect the rotation of a at least one shaft magnet 90 incorporated in the drive shaft 80. The shaft rotation sensor 86 or tachometer is discussed later in the detailed description following the details of the positioning features 16 of the control module 12.

Still referring to FIG. 3B, a detailed, projected view of the second side 18b of the control module 12 demonstrates additional positioning features 16 and complementary retention features 62 formed between the control module 12 and the drive-side interface 32. In the example shown, an annular opening or a receiving groove 94 may be formed along a perimeter edge 96 on the second side 18b of the control module 12 about the opening 68 formed by the collar 20. Opposite the second side 18b on the drive-side interface 32 of the drive head 28, a protrusion or positioning ring 98 may extend outward in a complementary mating configuration to the receiving groove 94. The positioning ring 98 and the receiving groove 94 may form a concentrically aligned interface spaced concentrically from the drive axis 78. As previously discussed, the alignment of the opening 68 with the coupling assembly 26 may provide for the drive shaft 80 to pass through the collar 20 and align with the drive coupling assembly 26 of the drive head 28 in the assembled configuration. This configuration of the encapsulated assembly 14 of the control module 12 with the coupling assembly 26 and the stator assembly 22 may enable a blind assembly operation of the corresponding drive and control assembly of the handpiece within the interior cavity formed by the housing 36.

As depicted in FIG. 1, when arranged in the assembled configuration, an elongated body 102 of the encapsulated assembly 14 may extend through the interior cavity 34 through a handle 104 from the drive body 106 or motor housing formed by the enclosure of the surgical handpiece 10. As further discussed in reference to FIG. 4, the elongated body 102 of the encapsulated assembly 14 may engage a wall or interior wall 108 formed in the handle 104 of the housing 36 of the surgical handpiece 10 via a fastener 110 (e.g., a mounting screw). The engagement of the fastener 110 to the interior wall 108 within the interior cavity 34 formed in the handle 104 may provide for the engagement of the receiving groove 94 of the control module 12 with the positioning ring 98 of the drive head 28. In this arrangement, the lobes or protrusions 64 within the interior cavity 34 may be aligned with the complementary receiving notches 66 formed on the stator interface 30 of the stator assembly 22 to ensure the stacked assembly of the control module 12 and the motor 24 is properly aligned with the interior cavity 34.

In addition to the physical engagement of the positioning features 16 with the complementary retention features 62, the conductive pins 76 of the stator assembly 22 may further engage the pin connectors 74 of the control module 12 to conductively connect the conductive interface 72. The engagement of the conductive interface 72 may be aligned between the first side 18a of the control module 12 and the stator interface 30 by sliding the stator assembly 22 of the motor 24 into the interior cavity 34 along the drive axis 78 extending through the drive body 106. The engagement of the positioning features 16 with the complementary retention features 62 may align the conductive interface 72 while also aligning the drive assembly (e.g., the output shaft 80) with the coupling assembly 26. As further demonstrated and discussed in reference to FIG. 4, the engagement of the collar 20 with the stator interface 30 and the drive-side interface 32 may be bound or locked in place upon the fixation of a fastening ring 120 and end cap 122 that engages the electric motor 24 and locks the positioning features 16 in contact with the complementary retention features 62 along the drive axis 78 of the surgical handpiece 10.

Referring generally to FIGS. 1-4, in various implementations, the encapsulated assembly 14 or potted assembly may correspond to one or more control circuits that may be implemented as circuit boards or printed circuit boards (PCBs) that are assembled or form a circuit assembly of the control module 12. The circuit assembly may form or be connected to a circuit frame or mounting structure that forms or otherwise provides an underlying mechanical structure forming the positioning features 16 of the control module 12. The resulting positioning features 16 provided by the encapsulated assembly 14 may be rigidly molded over the underlying PCBs and conductive contacts and/or provided by sealing portions of a circuit frame. The structure of the encapsulated assembly 14 may form a continuous, sealed assembly that may house or enclose one or more control circuits, sensor circuits, and switching or drive circuits within the encapsulated body of the control module 12. As discussed in the following examples, the circuits or features encapsulated within the potted or sealed assembly may comprise a trigger position sensor 46 (FIGS. 4 and 5), a shaft sensor 86 (FIGS. 3A and 3B), a controller 180 comprising a processor 182 and a memory 184, a motor controller 186 (FIG. 7), and/or various control circuits and sensors related to the operation of the surgical handpiece 10 as discussed herein.

The encapsulated assembly 14 may be enclosed or sealed via a potting process or conformal coating that may seal the encapsulated assembly 14 with a rigid or semi-rigid coating. The potting material or coating may correspond to a thermosetting plastic, silicone rubber, rubber gel, epoxy resin, or other mold substances that may be molded to provide for the elongated body, positioning features 16 and various attributes, structural or otherwise, of the encapsulated assembly. In some implementations, the underlying electrical or electronic components of the control module 12 may be encapsulated by placing the components in a mold, which is filled with an insulating compound that is cured to form the resulting features (e.g., the positioning features 16) discussed herein. In some implementations, the encapsulated assembly 14 may provide for or form the structure associated control module 12 (e.g., the positioning features 16, collar 20, elongated body 102, etc.). In this way, the encapsulation or potting of the control module 12 may provide for the structural alignment and connection to the handpiece 10 while also providing protection of sensitive electronic components from impact, vibration, and infiltration/corrosion related to use and sterilization of the surgical handpiece 10.

Figure 4:
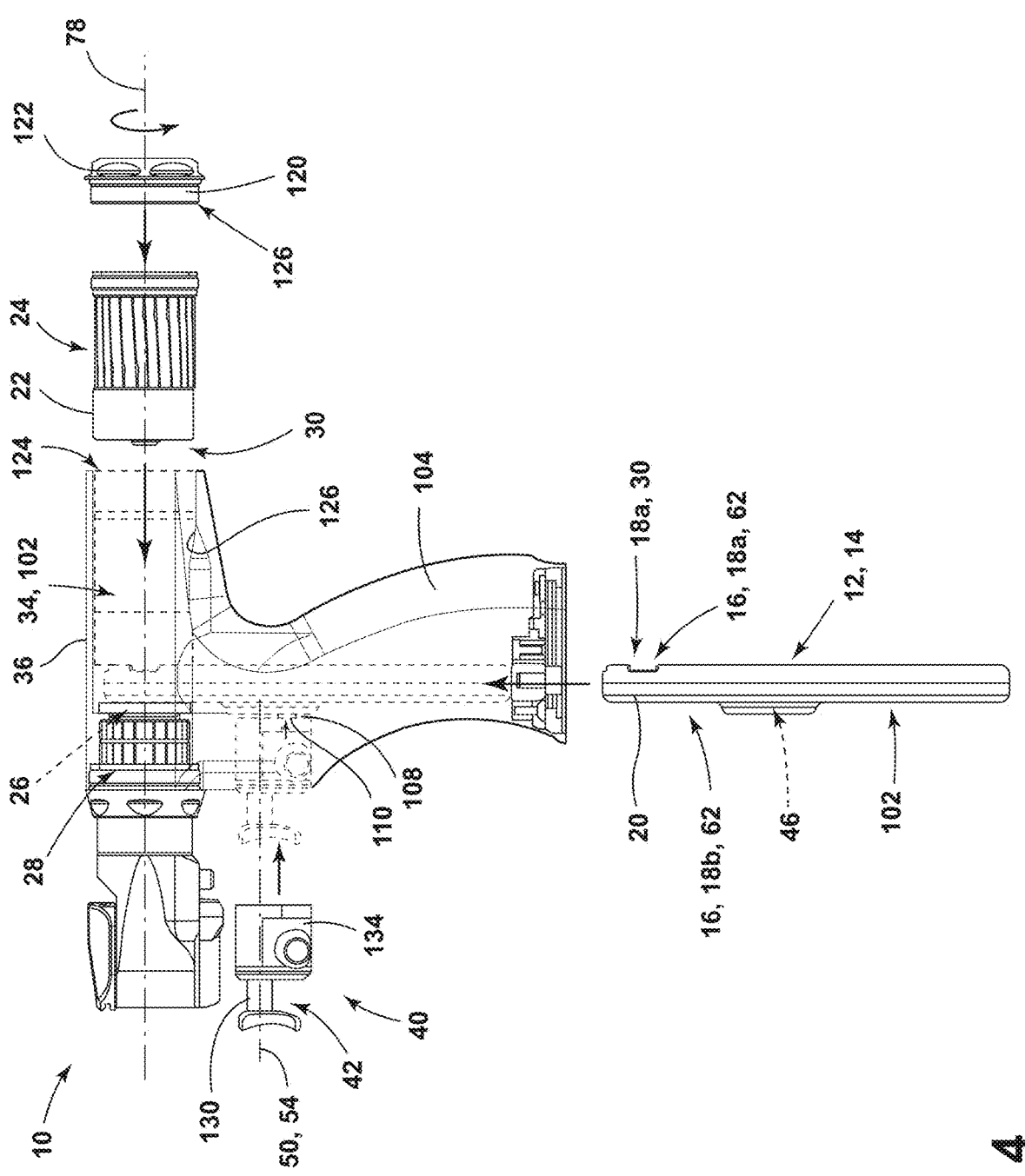
FIG. 4 is a partially-exploded assembly view of a surgical handpiece demonstrating an assembly method.

Referring now to FIG. 4, a partially exploded, assembly view of the surgical handpiece 10 is shown demonstrating the engagement of the control module 12 with the drive head 28 and the electric motor 24. As shown, the assembly of the surgical handpiece 10 may include installing the elongated body 102 of the control module 12 into the interior cavity 34 formed within the handle 104 and the housing 36. As previously discussed, the control module 12 may be aligned with the drive head 28 by engaging the positioning ring 98 of the drive-side interface 32 with the receiving groove 94 of the second side 18b of the control module 12. Additionally, the fastener 110 may bind the control module 12 within the handle 104, such that the alignment of the collar 20 is retained with the drive head 28 by the positioning features 16 and complementary retention features 62. In this configuration, the alignment of the control module 12 may be maintained within the body of the housing 36 while the handpiece 10 is reoriented to facilitate the installation of the stator assembly 22 and the motor 24.

With the control module 12 installed within the housing 36, the stator assembly 22 of the electric motor 24 may be guided through the interior cavity 34 extending along the drive body 106 along the drive axis 78. The stator assembly 22 of the electric motor 24 may be inserted into the interior cavity 34 within the drive body 106 until the receiving notches 66 of the stator interface 30 engage the lobes or protrusions 64 formed on the first side 18a of the collar 20. The insertion of the electric motor 24 into the interior cavity 34 formed by the drive body 106 may further include guiding the drive shaft 80 through the opening 68 formed in the collar 20, such that the drive shaft 80 engages the drive coupling assembly 26 (see FIG. 3B). With the electric motor 24 installed into the interior cavity 34, the collar 20 and the electric motor 24 may be secured in a rotationally and axially bound relationship in all degrees of freedom except along the drive axis 78. The translation along the drive axis 78 may be restrained by installing the fastening ring 120 and end cap 122 in connection with a distal assembly aperture 124 of the surgical handpiece 10. The fastening ring 120 may be secured to the drive body 106 within the distal assembly aperture 124 by a threaded or interlocking interface 126 that may be secured in place via a rotation of the end cap 122. In this configuration, the control module 12 may be secured in physical connection with the stator assembly 22 of the electric motor 24 within the surgical handpiece 10 and conductively connected to the stator interface 30 via the conductive interface 72. In this way, the design of the various components of the surgical handpiece 10 may provide for simplified assembly and alignment of each of the components to improve manufacture and service of the surgical handpiece 10.

Figure 5:
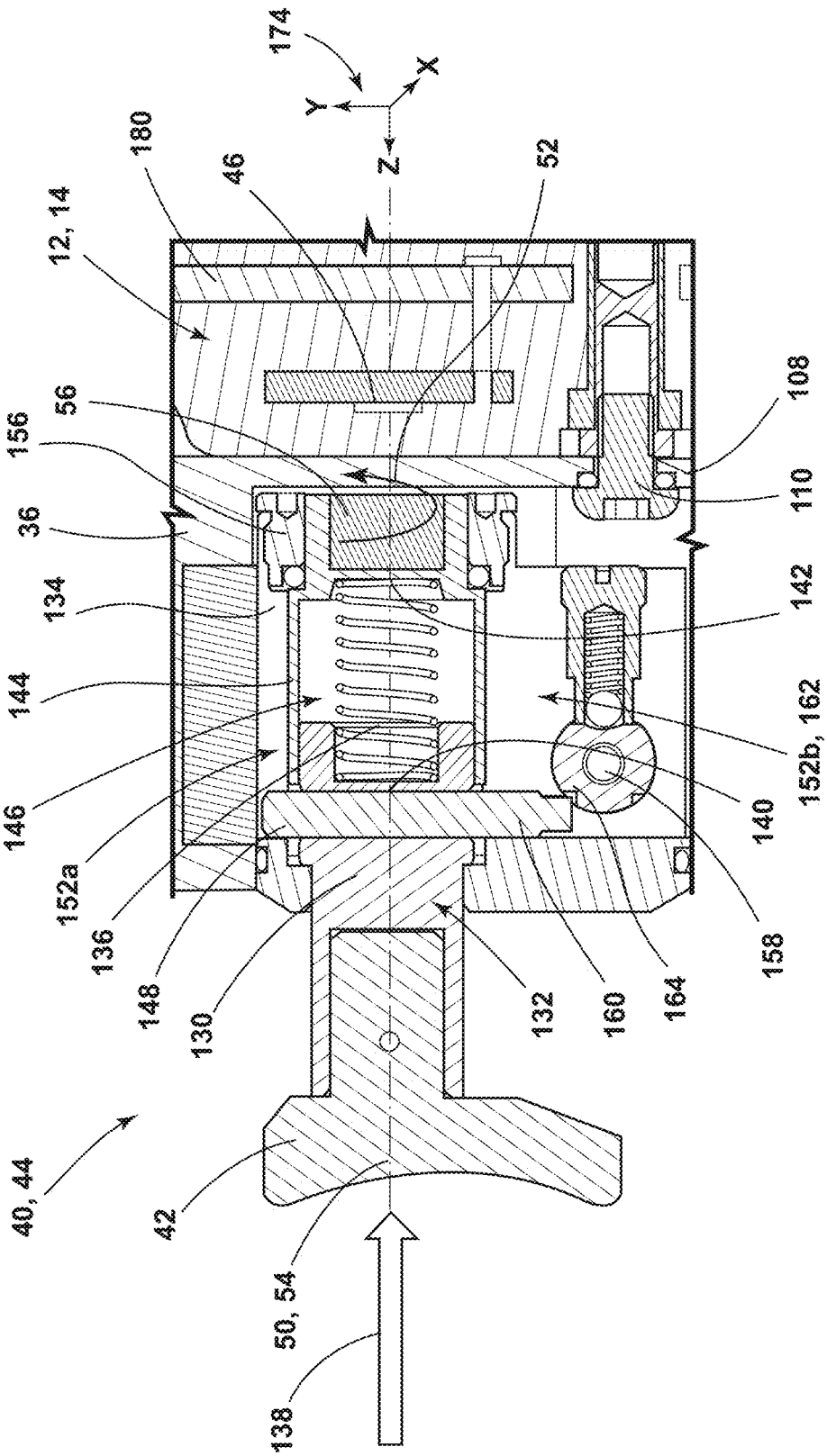
FIG. 5 is a side, cross-sectional view of an actuation mechanism for a surgical handpiece demonstrating a rotational linkage.

Referring now to FIG. 5, a side cross-sectional view of the actuation mechanism 40 is shown demonstrating the trigger assembly 42 and the rotational linkage 48. As previously discussed, the actuation mechanism 40 may be configured to adjust or rotate the orientation of the sensor magnet 56 in response to a translational input to the trigger assembly 42. In operation, the trigger assembly 42 may comprise a piston 130 that extends through a cylindrical opening 132 formed through a trigger housing 134 that engages a biasing spring 136. The biasing spring 136 may oppose a translational force 138, such that the trigger assembly 42 remains extended outward from the trigger housing 134 when at rest. The biasing spring 136 is seated between a receiving pocket 140 of the piston 130 and a compression surface 142 of a rotating collar or sleeve 144 forming the rotational linkage 48. As demonstrated in FIG. 5, the biasing spring 136 may extend along the trigger axis 54 through a cylinder 146 formed by the rotating collar or sleeve 144. In this arrangement, the depression of the trigger assembly 42 forces the piston 130 into the cylinder 146 and compresses the biasing spring 136. In addition to the compression of the biasing spring 136, the translation of the piston 130 may also drive or force a guide pin 148 of the rotational linkage 48 through a first guide channel 150 or a rotational guide channel formed in a wall of the rotating sleeve or collar 144. As further discussed in reference to FIGS. 6A-6C, the translational motion of the trigger assembly 42 and the resulting engagement of the guide pin 148 within the first guide channel 150 may result in the rotation of the rotating collar 144 and resulting rotation of the sensor magnet 56.

Referring now to FIGS. 5 and 6A-6C, the guide pin 148 may extend from a first side 152*a* of the trigger assembly 42 into a second guide channel 154 formed in or through a wall of the trigger housing 134. The second guide channel 154 may correspond to a translational guide channel that may be engaged by an upper distal end of the guide pin 148 that extends into the first guide channel 150. Opposite the first side 152*a*, the guide pin 148 may further extend through the piston 130 outward to a second side 152*b* of the trigger assembly 42. In this configuration, the depression of the trigger assembly 42 may cause the piston 130 to force the guide pin 148 along the second guide channel 154, resulting in the rotation of the rotating collar 144 in response to the intersection of the guide pin 148 with the first or rotational guide channel 150. In order to ensure that the rotation of the rotating collar 144 actuates smoothly as a result of the pressure applied by the guide pin 148, the rotating collar 144 of the rotational linkage 48 may be supported in connection with the trigger housing 134 via a rotary bearing 156 at a distal end. The rotary bearing 156 may be connected to the distal end of the rotating collar 144 opposite a proximal end supported by the piston 130 of the trigger assembly 42. In this configuration, the rotating collar 144 may smoothly rotate within the rotary bearing 156, thereby providing for the rotation of the sensor magnet 56, the orientation of which may then be detected by the position sensor 46 of the control module 12.

Within the trigger housing 134 on the second side 152*b* of the trigger assembly 42, the actuation mechanism 40 may further comprise a locking cylinder 158 that can be selectively disengaged (translated transversely relative to the trigger axis 54) to allow a free end 160 of the guide pin 148 to translate along the trigger axis 54. As shown, the guide pin 148 may extend from the second side 152*b* or a bottom portion of the trigger assembly 42 into a cavity 162 within the trigger housing 134. The locking cylinder 158 may extend across or transverse to the trigger axis 54 and selectively position a protrusion or locking tab 164 to intersect with the translational path of the guide pin 148, thereby blocking or preventing the compression of the trigger assembly 42 and any resulting activation of the surgical handpiece 10. In this way, the actuation mechanism 40 may be locked to prevent activation of the surgical handpiece 10.

Figures 6A, 6B, 6C:
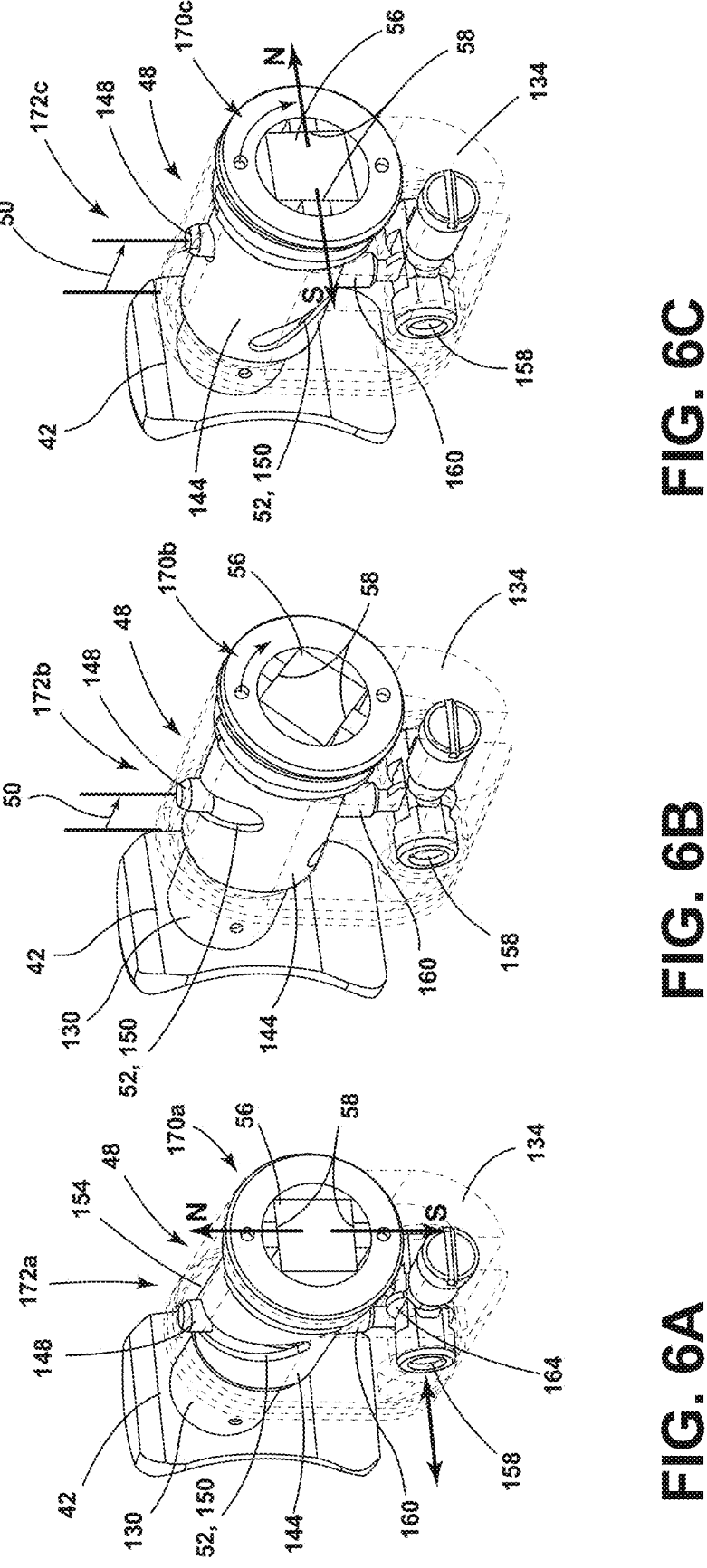
FIG. 6A is a projected view demonstrating a trigger assembly of an actuation mechanism for a surgical handpiece in a first position.
FIG. 6B is a projected view demonstrating a trigger assembly of an actuation mechanism for a surgical handpiece in a second position.
FIG. 6C is a projected view demonstrating a trigger assembly of an actuation mechanism for a surgical handpiece in a third position.

Referring now to FIGS. 6A-6C, the sensor magnet 56 is demonstrated in a plurality of sequential, rotational orientations 170*a*, 170*b*, 170*c* in response to an increasing depression or translation of the trigger assembly 42. As shown in FIG. 6A, the piston 130 is extended outward to a resting position by the biasing spring 136. In this configuration, the guide pin 148 is positioned in a forward position along the first guide channel 150 and the second guide channel 154. In the example shown, the exemplary poles 58 of the sensor magnet 56 are oriented such that a first pole 58*a* or north pole is facing the first side 152*a* of the trigger assembly 42 and the second pole 58*b* is oriented facing the second side 152*b* of the trigger assembly 42. Though the orientation of the sensor magnet 56 is described in the example shown, it shall be understood that the relative orientation of the sensor magnet 56 may vary while achieving similar sensory functions.

In each of FIGS. 6B and 6C, the trigger assembly 42 is demonstrated as being compressed over an increasing distance of the translational path 50 resulting in an increasing rotation of the poles 58 of the sensor magnet 56 about the trigger axis 54. The representations of the actuation mechanism 40 shown in FIGS. 6A-6C demonstrate the trigger assembly 42 and the piston 130 located in a first translational position 172*a*, a second translational position 172*b*, and a third translational position 172*c* extending along the translational path 50. In response to the movement of the guide pin 148 along the translational path 50, the rotating collar 144 may adjust the rotational orientation 170 of the sensor magnet 56 to a first rotational orientation 170*a*, a second rotational orientation 170*b*, and a third rotational orientation 170*c* that respectively correspond to the first translational position 172*a*, the second rotational position 172*b*, and the third rotational organization 172*c*. As a result of the travel of the trigger assembly 42 along the translational path 50, the sensor magnet 56 and the corresponding poles 58 may rotate over a range of angles that may be defined by a pitch or angle of the rotational path 52 formed by the first or rotational guide channels 150 of the rotating collar 144. In the specific example shown, the travel of the trigger assembly 42 over the translational path 50 may result in rotation of the sensor magnet 56 from approximately 0° to 90°. However, the rotation of the sensor magnet 56 may similarly be adjusted over ranges of 30°, 45°, 60°, 120°, ° 180, etc. based on the travel of the trigger assembly 42 as well as the pitch of the rotational path 52. In any case, responsive to such a rotation, as better demonstrated in FIG. 1, the position sensor 46 may wirelessly detect the positioning indication identified by the orientation of the poles 58 of the sensor magnet 56 to control the actuation of the surgical handpiece 10.

In order to accomplish the detection of the orientation of the poles 58 of the magnet 56, the position sensor 46 may correspond to a multi-dimensional (e.g., two-dimensional or three-dimensional) magnetic flux density sensor. As shown in FIG. 5, the position sensor 46 may detect the rotational orientations 170 of the poles 58 of the sensor magnet 56 as they rotate about the trigger axis 54 in response to the depression of the trigger assembly 42. For example, the position sensor 46 may wirelessly detect the orientation of the sensor magnet 56 rotating about an exemplary Z-axis by identifying a directional flux density in a perpendicular X-Y plane of a coordinate system 174. In this way, the position sensor 46 may detect the orientation of the poles 58 of the sensor magnet 56 as they rotate about the drive axis 78 without requiring any translational motion of the sensor magnet 56 along the translational path 50 of the trigger assembly 42. Such an arrangement of the position sensor 46 and the sensor magnets 56 provided by the actuation mechanism 40 may improve the accuracy and sensitivity of the measurement of the depression of the trigger assembly 42.

Figure 7:
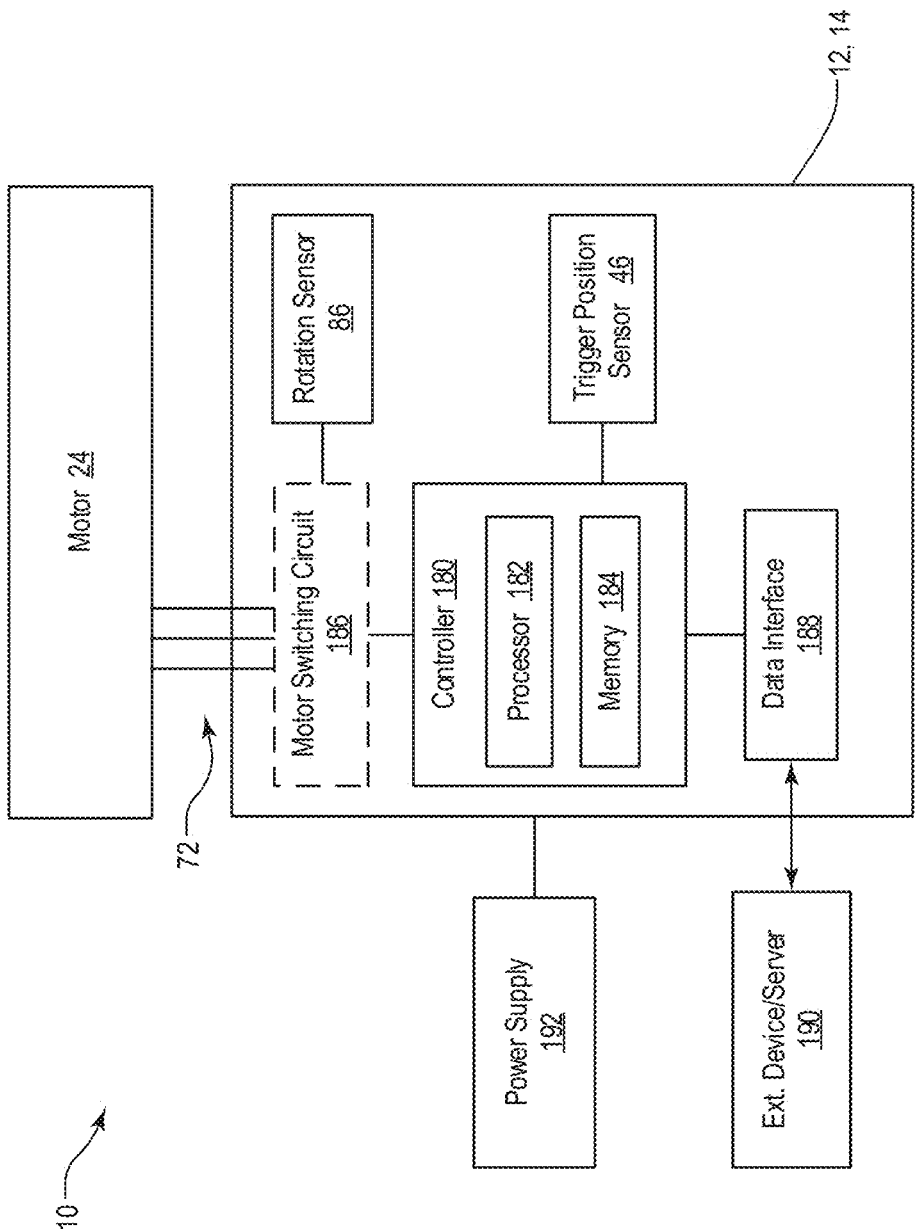
FIG. 7 is a block diagram of a surgical handpiece in accordance with the disclosure.

Referring now to FIG. 7, the operation of the motor 24 of the surgical handpiece 10 may generally be provided by instructions identified by a controller 180 of the control module 12. In various implementations, the controller 180 may comprise one or more processors 182 and a memory 184 or memory devices. In various embodiments, the processor 182 may correspond to a digital signal processor (DSP) that may be integrated in the control module 12 as an application specific integrated controller (ASIC) or other forms of processing circuits, processors, microcontrollers, etc. The memory 184 may be configured to store various program instructions that control the operation of the handpiece 10 in response to various user inputs, for example, inputs to the position sensor 46 as discussed herein. The memory 184 may comprise various forms of data or instruction storing technologies, including volatile and/or non-volatile memory that may include read-only memory (ROM), erasable/programmable read-only memory (EPROM), electronically erasable/programmable ROM (EEPROM), random access memory (RAM), etc. In operation, the memory 184 may store program instructions and routines that may be followed by the processor 182 to output control signals to a motor switching or control circuit 186 or motor controller in response to signals received from the position sensor 46.

In various implementations, the controller 180 may comprise a data interface 188 (e.g., serial communication bus) that may be configured for communication with an external device 190 or server. The communication via the data interface may provide for updates to various control routines or settings stored in the memory 184. In this way, the programming and operation of the surgical handpiece 10 may be modified and/or monitored by controlling the instructions communicated to a motor switching or control circuit 186 and identifying operating statistics for the handpiece 10 stored in the memory 184 and accessed via the external device 190. As previously discussed in reference to FIG. 3B, the operation of the motor 24 may be monitored by the motor control circuit 186 via the rotation sensor 86. The rotation sensor 86 may comprise the magnetic sensor array 88 (e.g., an array of Hall effect sensors) that may be radially positioned in the collar 20 about the drive axis 78 of the motor 24. In response to the rotation of the drive shaft 80, the rotation of the one or more shaft magnets 90 and the corresponding magnetic fields rotating within the magnetic sensor array 88 may be detected and communicated as rotational or tachometer signals to the motor control circuit 186. In this way, the rotation sensor 86 may identify the rotational position of the motor 24 and provide feedback regarding the rotational speed of the drive shaft 80. Finally, the operation of the control module 12 and the motor 24 of the surgical handpiece 10 may be supplied with operating current via a power supply 192 that may correspond to a hardwired power supply, rechargeable battery pack, or various other power supply technologies.

As discussed in the previous detailed description, the disclosure provides for a variety of beneficial features to improve the operation, assembly, and repair of the surgical handpiece 10. It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents The claims:

1. An actuation mechanism for a surgical handpiece, the mechanism comprising:
   a trigger assembly extending along a translational path;
   a rotational linkage in connection with the trigger assembly that converts translational motion along the translational path to a rotational motion about an actuation path; and
   a magnet in connection with the rotational linkage, wherein the magnet comprises opposing poles that rotate in response to the rotational motion.

2. The actuation mechanism according to claim 1, further comprising a housing enclosing at least a portion of the trigger assembly and the rotational linkage.

3. The actuation mechanism according to claim 2, wherein the housing comprises a guide channel configured to receive the guide pin, wherein the translational path of the trigger assembly is defined by the guide channel.

4. The actuation mechanism according to claim 3, wherein the trigger assembly comprises a piston and the translational motion of the piston is guided along the translational path defined by the guide channel by an engagement of the guide pin with the guide channel.

5. The actuation mechanism according to claim 3, wherein the rotational linkage further comprises:
   a rotary bearing interconnecting a rotating collar to a first end portion of the housing.

6. The actuation mechanism according to claim 1, further comprising:
   a biasing spring that compresses along the translation path in response to pressure applied to the trigger assembly.

7. The actuation mechanism according to claim 1, wherein the trigger assembly comprises a piston that extends into a cylinder formed by a rotating collar of the rotational linkage.

8. The actuation mechanism according to claim 7, wherein the piston compresses a biasing spring within the cylinder in response to the translational motion.

9. The actuation mechanism according to claim 7, further comprising:
   a guide pin extending transversely from the piston.

10. The actuation mechanism according to claim 9, wherein the guide pin engages an elongated opening extending through the rotating collar, wherein the elongated opening forms a guide path extending at an angle about the translational path of the trigger assembly.

11. The actuation mechanism according to claim 10, wherein the guide pin slidably engages a wall of the elongated opening in response to the translation motion of the piston.

12. The actuation mechanism according to claim 11, wherein, in response to the engagement of the guide pin with the wall, the rotating collar rotates about the piston causing the rotation of the opposing poles of the magnet.

13. The actuation mechanism according to claim 11, wherein the elongated opening forms a helical path and the angle relative to the actuation path defines a pitch of the helical path.

14. The actuation mechanism according to claim 1, wherein the actuation mechanism is located adjacent to a magnetic sensor in communication with a control circuit of the surgical handpiece, wherein the magnetic sensor is configured to detect an orientation of the magnet.

15. The actuation mechanism according to claim 14, wherein the magnetic sensor is disposed outside the housing and separated from the magnet via a sealed enclosure of the handpiece.

16. A method for actuating a surgical handpiece, the method comprising:

receiving a translational input along a trigger axis via a trigger assembly;

converting the translation input to a rotational output about a rotary axis parallel to the trigger axis;

rotating a plurality of poles of a sensor magnet with the rotational output;

detecting a direction of the poles of the sensor magnet; and in response to a change in the direction of the poles, activating an adjustable setting of the surgical handpiece.

17. The method according to claim 16, wherein the converting of the translational input to the rotational output comprises:

guiding a pin of the trigger assembly along a translation path extending along the trigger axis.

18. The method according to claim 17, wherein the converting of the translational input to the rotational output further comprises:

engaging a helical path with the pin of the trigger assembly.

19. The method according to claim 18, further comprising:

rotating the plurality of poles of the sensor magnet about the rotary axis at a rate of rotation defined by a pitch of the helical path.

20. An actuation mechanism for a surgical handpiece, the actuation mechanism comprising:

a trigger assembly comprising a piston and a guide protrusion extending from a surface of the piston, wherein the piston is configured to translate along a trigger axis;

a first guide slot formed in a housing of the actuation mechanism extending parallel to the trigger axis and configured to receive the guide protrusion;

a second guide slot formed by a rotational linkage and extending about the trigger axis at a pitch; and a sensor element in connection with the rotational linkage, wherein the sensor element is rotated by the rotational linkage about the trigger axis in response to the translation of the piston along the trigger axis.

21. The actuation mechanism according to claim 20, wherein a rate of rotation is defined by the pitch.

22. The actuation mechanism according to claim 20, wherein the first guide slot is formed in a housing of the actuation mechanism and wherein the rotational linkage comprises a sleeve forming a cylinder, wherein the sleeve rotates within the housing in response to a translation of the piston along the trigger axis.

23. The actuation mechanism according to claim 22, wherein the sleeve is in connection with the housing via a rotary bearing aligned perpendicular to the trigger axis.

24. The actuation mechanism according to claim 20, wherein the sensor element is a magnet comprising a plurality of poles, wherein a rotational orientation of the plurality of poles of the sensor element is detected by a magnetic sensor separated from the magnet by a sealed wall of a control circuit.

25. The actuation mechanism according to claim 24, wherein the rotational orientation is identified by a control circuit of the surgical handpiece, and a drive of a motor of the handpiece is variably controlled in response to the rotational orientation.

\* \* \* \* \*